United States Patent
Edgar

(10) Patent No.: US 9,615,183 B2
(45) Date of Patent: Apr. 4, 2017

(54) METHOD AND APPARATUS FOR TAGGING PATIENT SESSIONS FOR FITTING HEARING AIDS

(75) Inventor: Dan Edgar, Lakeville, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 1747 days.

(21) Appl. No.: 12/543,139

(22) Filed: Aug. 18, 2009

(65) Prior Publication Data

US 2011/0044482 A1 Feb. 24, 2011

(51) Int. Cl.
H04R 29/00 (2006.01)
H04R 25/00 (2006.01)
A61B 5/12 (2006.01)

(52) U.S. Cl.
CPC .............. *H04R 25/70* (2013.01); *A61B 5/121* (2013.01); *H04R 25/30* (2013.01)

(58) Field of Classification Search
CPC ........... A61B 5/12; A61B 5/121; A61B 5/123; A61B 5/125; H04R 25/00; H04R 25/30; H04R 25/50; H04R 25/70; H04R 25/305; H04R 25/502; H04R 25/505; H04R 25/507
USPC ......... 381/60, 23.1, 312, 313–321; 600/559; 73/585
See application file for complete search history.

(56) References Cited

U.S. PATENT DOCUMENTS

| | | | |
|---|---|---|---|
| 7,349,549 B2 * | 3/2008 | Bachler ................ | H04R 25/305 381/314 |
| 7,366,307 B2 * | 4/2008 | Yanz et al. ...................... | 381/60 |
| 2004/0213424 A1 | 10/2004 | Hamacher et al. | |
| 2006/0093997 A1 | 5/2006 | Kearby et al. | |
| 2008/0037798 A1 * | 2/2008 | Baechler et al. ............... | 381/60 |

FOREIGN PATENT DOCUMENTS

| | | | |
|---|---|---|---|
| WO | WO-2005125282 A2 | 12/2005 | |
| WO | WO-2006136616 A2 | 12/2006 | |
| WO | WO 2008/151625 * | 12/2008 | ............. H04R 25/00 |
| WO | WO-2008151625 A1 | 12/2008 | |
| WO | WO-2011022385 A1 | 2/2011 | |

OTHER PUBLICATIONS

"International Application Serial No. PCT/US2010/045743, Search Report mailed Nov. 8, 2010", 7 pgs.
"International Application Serial No. PCT/US2010/045743, Written Opinion mailed Nov. 8, 2010", 6 pgs.
"European Application Serial No. 10747754.9, Amended Claims Response filed Oct. 15, 2012", 9 pgs.
"European Application Serial No. 10747754.9, Examination Notification Art. 94(3) mailed Jul. 12, 2013", 4 pgs.
"European Application Serial No. 10747754.9, Office Action mailed Jan. 25, 2013", 6 pgs.
"European Application Serial No. 10747754.9, Response filed May 28, 2013 to Office Action mailed Jan. 25, 2013", 7 pgs.

* cited by examiner

*Primary Examiner* — Xu Mei
(74) *Attorney, Agent, or Firm* — Schwegman Lundberg & Woessner, P.A.

(57) ABSTRACT

The present subject matter relates generally to the method and apparatus for storing tags during a fitting session. The tags may be used to store information useful for an audiologist, a manufacturer of hearing aids, and a manufacturer of fitting software. The software adapted to provide searching based on tags. The software able to provide pre-programmed tags for use by the user. In various applications the software programmable to automatically generate tags upon occurrence of one or more conditions.

23 Claims, 1 Drawing Sheet

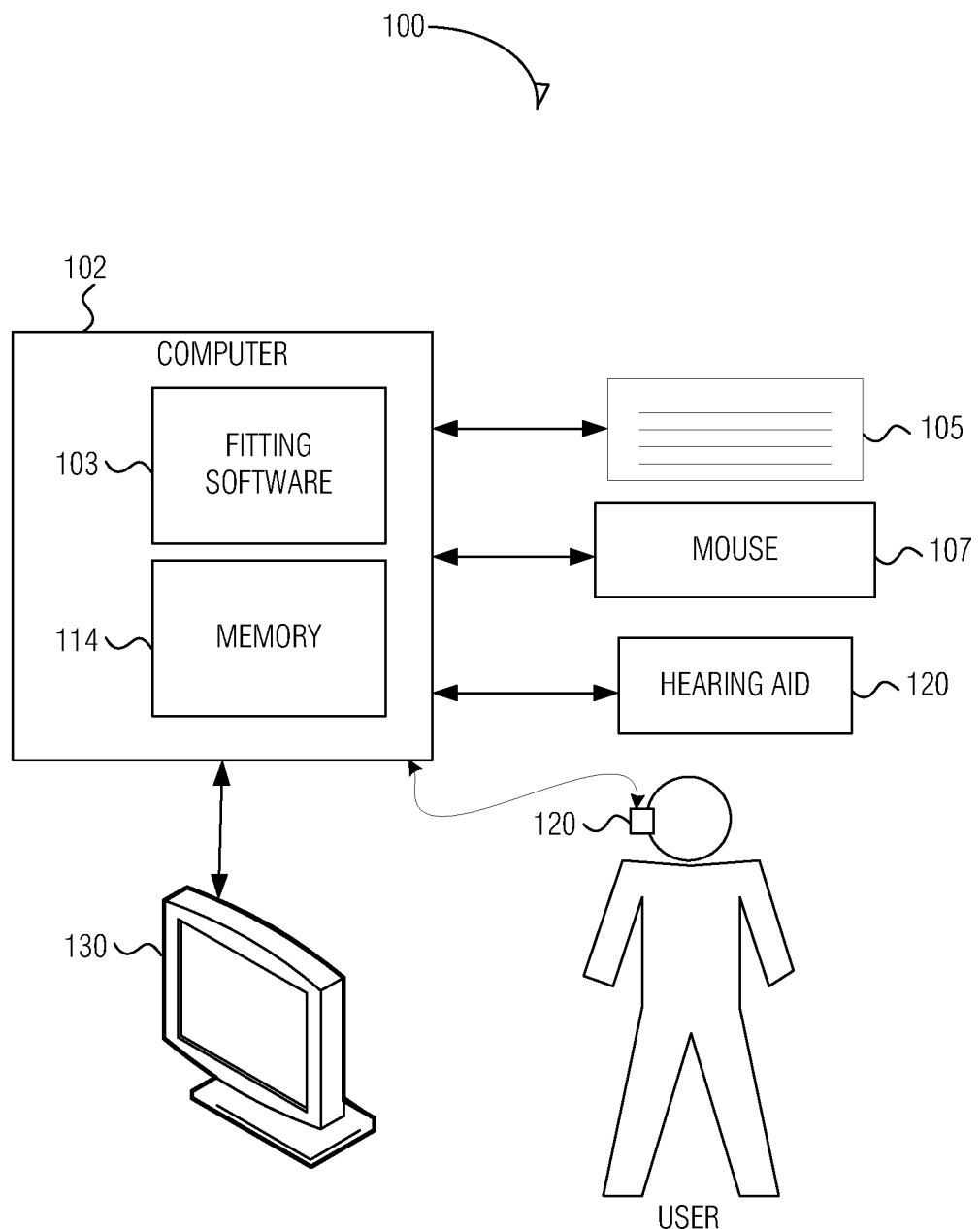

METHOD AND APPARATUS FOR TAGGING PATIENT SESSIONS FOR FITTING HEARING AIDS

FIELD OF THE INVENTION

The present subject matter relates generally to fitting hearing aids, and in particular to method and apparatus for tagging patient sessions for fitting hearing aids.

BACKGROUND

Wearers of hearing aids undergo a process called "fitting" to adjust the hearing aid to their particular hearing and use. In such fitting sessions the wearer may select one setting over another, much like selecting one setting over another in an eye test. Other types of selections include changes in level, which can be a preferred level. A hearing aid fitting session may involve several attempts at fitting the aids or may be uneventful. The clinician or audiologist may experience some events or conditions that would be useful to know for later fittings. Thus, there is a need in the art for improved communications for performing fitting.

SUMMARY

Disclosed herein, among other things, are methods and apparatus for method and apparatus for tagging patient sessions for fitting hearing aids. The tags may be used to store information useful for an audiologist, a manufacturer of hearing aids, and a manufacturer of fitting software. In various applications, the system is adapted to provide searching based on tags. The software able to provide pre-programmed tags for use by the user. In various applications the software programmable to automatically generate tags upon occurrence of one or more conditions.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

FIG. 1 shows a fitting system providing tagging according to various embodiments of the present subject matter.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter of the invention relates generally to method and apparatus for tagging patient sessions when fitting hearing aids. A hearing aid fitting system is typically controlled via standard mouse and keyboard input. These audiologist or dispenser has access to a mouse and keyboard while tending to a patient.

FIG. 1 shows a fitting system with gesture sensing according to various embodiments of the present subject matter. Computer 102 is adapted to execute fitting software 103 that takes typical inputs from devices such as keyboard 105 and mouse 107 for fitting one or more hearing aids 120. It is understood that the user may be the wearer of one or more hearing aids or can be a clinician, audiologist or other attendant assisting with the use of the fitting system 100. The system 100 includes memory 114 which stores and displays on display 130 one or more tags for the fitting system. It is understood that the configuration shown in FIG. 1 is demonstrative and is not intended in an exhaustive or exclusive sense. Other configurations may exist without departing from the scope of the present subject matter. For example, it is possible that the memory 114 may be encoded in firmware, software, or combinations thereof. It is possible that the system may omit a mouse or a keyboard or may include additional input/output devices without departing from the scope of the present subject matter. Other variations are possible without departing from the present subject matter.

The present subject matter allows an end user to associate one or more word tags to a fitting session in hearing aid fitting software. In various embodiments, these tag values may be used by the fitting software manufacturer, the hearing aid manufacturer, the hearing aid fitting professional, and others to evaluate the effectiveness of a fitting for patients and/or the efficacy of the hearing aid itself. In various embodiments, the tag values are associated to different aspects of the hearing aid product being fit. For example, such associations include, but are not limited to, one or more of the particular hearing aid being fit, the adjustments made, the audiogram of the patient, fitting formula and/or other fitting session parameter values. It is understood that the information may be made anonymous to protect the privacy of the patient.

In various applications, the tags are pre-populated with values including, but not limited to, examples such as: Effective, Ineffective, Follow Up Visit, First Visit, Requires Follow Up, 1 Star Rating, 2 Star Rating, 3 Star Rating, 4 Star Rating, 5 Star Rating, Easy Fit, and/or Difficult Fit.

In various embodiments of the present subject matter, the user is prompted to tag the fitting at the time they save the fitting session. In various embodiments of the present subject matter, the user can save tags as desired and at any time. In various embodiments of the present subject matter, the system is programmable to automatically tag when certain conditions occur. For example, an automatic tag can be generated when a hearing aid is not fitted within a certain predetermined amount of time. For example, if a particular fitting screen is active for over 20 minutes, the system can automatically tag the fitting as involving potentially improper hearing aid selection. Other automatic tags are possible, such as if an Active Feedback Intercept is used more than a predetermined number of times, the aid can be flagged as being a high return risk. For example, the system can automatically flag the fitting session and the aid if Active Feedback Intercept is used more than two times. These examples are given to demonstrate the present subject matter. It is understood that other fitting parameters, limits, settings, and conditions may be used to automatically tag a fitting session and/or hearing aid, and the present subject matter is not limited by the examples given herein.

In various embodiments the user can search fittings based on their tags. The open session screen will be augmented with a tag list that allows the end user to look at fittings that were tagged with their tags.

The user can also opt in to a "Customer Improvement Program" where their tags and anonymous fitting session data will be uploaded to the hearing aid manufacturer via the Internet to assist the hearing aid manufacturer in improving the fitting software for future releases.

In various applications the tags are used to alert the user to other high rated fitting sessions based on fitting session variables. This alert system is programmable to save time spent with a patient and allow an audiologist to create libraries of good fittings that they can apply to their patient base.

The tags can also be used to store feedback from the users of the fitting software.

In various embodiments, a fitting system is adapted to perform the present subject matter disclosed herein. In various embodiments, the tagging is performed by an interface for a fitting system for performing the tagging discussed herein. It is understood that the present subject matter can be used with a variety of fitting systems including present systems and future fitting systems.

The present subject matter is demonstrated in the fitting of hearing aids, including but not limited to, behind-the-ear (BTE), in-the-ear (ITE), in-the-canal (ITC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user. The present subject matter can also be used in hearing assistance devices generally, such as cochlear implant type hearing devices. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method for fitting a hearing aid worn by a wearer with a fitting system, comprising:
    programming an interface of the fitting system adapted to store a plurality of word tags, the tags pre-populated with values for association with a fitting session parameter value, the interface adapted for input of entries of at least one of the plurality of tags by a user of the fitting system during a fitting session and to store the at least one of the plurality of tags associated with the fitting session, wherein the at least one of the plurality of tags includes one or more words of searchable text to describe an evaluation by the user of effectiveness of the fitting session.

2. The method of claim 1, further comprising searching on one or more of the plurality of tags.

3. The method of claim 1, further comprising downloading tag information to a manufacturer of the hearing aid.

4. The method of claim 1, further comprising downloading anonymous tag information to a manufacturer of the hearing aid.

5. The method of claim 1, further comprising downloading tag information to a maker of the fitting software.

6. The method of claim 1, further comprising downloading anonymous tag information to a maker of the fitting software.

7. The method of claim 1, wherein the tags are pre-populated.

8. The method of claim 7, wherein the pre-populated tags include one or more of Effective, Ineffective, Follow Up Visit, First Visit, Requires Follow Up, 1 Star Rating, 2 Star Rating, 3 Star Rating, 4 Star Rating, 5 Star Rating, Easy Fit, and/or Difficult Fit.

9. The method of claim 8, further comprising prompting the user to tag the fitting session.

10. The method of claim 1, further comprising prompting the user to tag the fitting session.

11. The method of claim 1, further comprising programming the interface to automatically generate a tag upon occurrence of one or more programmed conditions.

12. The method of claim 1, further comprising downloading tag information over the INTERNET.

13. The method of claim 1, further comprising using the tags to alert the user to one or more successful fittings.

14. The method of claim 1, further comprising storing user feedback from use of the fitting software using the tags.

15. The method of claim 1, further comprising prompting the user to save a tag when storing the fitting session.

16. A fitting system for fitting a hearing aid, the fitting system executing on a computer, the system comprising:
    an input device for association of one or more word tags with a fitting session by a user of the fitting system during the fitting session, the one or more word tags pre-populated with values for association with a fitting session parameter value, wherein at least one of the tags includes one or more words of searchable text to describe an evaluation by the user of effectiveness of the fitting session;
    memory to store the one or more tags associated with the fitting session; and
    a display of the one or more tags for the users of the fitting system,
    wherein the computer is adapted to store and display the one or more tags.

17. The system of claim 16, wherein the computer is adapted to search the one or more tags.

18. The system of claim 16, wherein the computer is adapted to communicate the one or more tags over a network.

19. The system of claim 18, wherein the network is the INTERNET.

20. The system of claim 16, wherein the computer is adapted to provide pre-populated tags to the user for tagging a patient session.

21. The system of claim 16, wherein the computer is programmed to prompt the user to enter the one or more tags.

22. The system of claim 16, wherein the computer is programmed to store tags upon storing a fitting session.

23. The system of claim 16, wherein the computer is programmed to automatically produce tags upon occurrence of one or more conditions.

* * * * *